United States Patent [19]

Wagner et al.

[11] Patent Number: 5,508,442

[45] Date of Patent: Apr. 16, 1996

[54] REACTOR AND CONTINUOUS PROCESS TO BE CARRIED OUT THEREWITH FOR THE PREPARATION OF ETHYLENE GLYCOL CARBONATE AND PROPYLENE GLYCOL CARBONATE

[75] Inventors: Paul Wagner, Düsseldorf; Christine Mendoza-Frohn, Erkrath; Hans-Josef Buysch, Krefeld, all of Germany

[73] Assignee: Bayer Aktiengesellschaft, Leverkusen, Germany

[21] Appl. No.: 251,229

[22] Filed: May 31, 1994

[30] Foreign Application Priority Data

Jun. 7, 1993 [DE] Germany ............... 43 18 893.1

[51] Int. Cl.⁶ ............... C07D 321/00; C07D 323/00; C07D 317/38
[52] U.S. Cl. ............... 549/228; 549/229; 549/230
[58] Field of Search ............... 549/228, 229, 549/230

[56] References Cited

U.S. PATENT DOCUMENTS 4,314,945   2/1982   McMullen et al. ............... 549/228

FOREIGN PATENT DOCUMENTS

| 0546428 | 6/1993 | European Pat. Off. . |
| 2855232 | 6/1979 | Germany . |
| 172342 | 7/1965 | U.S.S.R. . |

OTHER PUBLICATIONS

Schulze, Chem. Abst. 78–6020 (1972).
Extrait de Brevet Russe (Derwent), Russian Patent No. 172,342; one page; "Method for the prepn. of Alkylene Carbonates". (1965).
Japanese Abstract, vol. 6, No. 197, 1 page, C–128, Oct. 6, 1982; "Preparation of Alkylene Glycol", Nippon Shokubai Kagaku Kogyo KK, K. Arasaki; 57–106631(A).
Chemical Abstracts, vol. 99, 1983, p. 102; CA #141920f: "Thermostatted reactor for ethylene carbonate synthesis", M. Scurtu.
Chemi–Ingenieur–Techn., vol. 43, No. 16, 1971; "Athylen–und Propylencarbonat", G. Hechler, pp. 903–905.
Industrial and Engineering Chemistry, vol. 50, No. 5, 5/1958, pp. 767–770; "Preparation and Properties of the Alkylen Carbonates", W. J. Peppel.
Fette–Seifen–Anstrichmittel, vol. 76, No. 6, 1971, pp. 396–399; "Die Technishe Herstellung von Athylencarbonat", H. Pringmann.

*Primary Examiner*—Cecilia Tsang
*Attorney, Agent, or Firm*—Sprung Horn Kramer & Woods

[57] ABSTRACT

A bubble column reactor is described which is characterized by a slenderness ratio at a ratio of height to diameter of 2 to 50, a feed, at the bottom end of the bubble column, for the ethylene glycol carbonate (EGG) or propylene glycol carbonate (PGC) already present serving as reaction medium, one or more metering sites for the starting materials $CO_2$ and ethylene oxide (EOX) or propylene oxide (POX) above the feed for the reaction medium, an outlet for the reaction mixture at the top end of the bubble column, a dividing apparatus connected thereto for the reaction mixture flowing off for dividing it into reaction mixture to be taken off and worked up on the one hand and reaction mixture to be recycled on the other hand and additionally a return line to the feed for the reaction mixture to be recycled. This bubble column reactor can be advantageously used in a process for the continuous preparation of EGG or PGC which is carried out in the temperature range from 100° to 200° C., in the pressure range from 5 to 200 bar and at a molar ratio of 1.01 to 1.5 mol of $CO_2$ per mol of alkylene oxide in EGG or PGC already present as reaction medium in an amount which is 7 to 350 times that of the newly formed EGG or PGC.

20 Claims, 1 Drawing Sheet

REACTOR AND CONTINUOUS PROCESS TO BE CARRIED OUT THEREWITH FOR THE PREPARATION OF ETHYLENE GLYCOL CARBONATE AND PROPYLENE GLYCOL CARBONATE

BACKGROUND OF THE INVENTION

1. Field of the Invention

The present invention relates to a bubble column reactor and a process to be carried out therewith for the preparation of ethylene glycol carbonate (EGC) or propylene glycol carbonate (PGC) by reaction of $CO_2$ with ethylene oxide (EOX) or propylene oxide (POX) in EGC or PGC already present as reaction medium. The execution of the said process in the bubble column reactor provided according to the invention proceeds particularly mildly for the reaction partners and the catalyst to be used, since side reactions of the EOX or POX used can be substantially minimized. This results through a high selectivity of the reaction of EOX or POX with $CO_2$. From this there results an energy- and material-saving process. The reaction is preferably carried out adiabatically.

2. Description of the Related Art

The preparation of EGC or PGC from $CO_2$ and EOX or POX, respectively, has long been known. Many publications in this area relate especially to the use of certain catalysts. A detailed presentation of this can be found in Fette, Seifen, Anstrichmittel 73 (1971), 396. Additional publications are, for example, Ind. Eng. Chem. 50 (1958), 767, Chem. Ing. Techn. 43 (1971), 903 and German Offenlegungsschrift 28 55 232 (equivalent to U.S. Pat. No. 4,314,945).

The process described in Ind. Eng. Chem. (loc. cit.) for the preparation of EGC or PGC in the presence of tetraethylammonium bromide as catalyst is carried out at 180° C. and 100 bar in a pumped circulation reactor. This pumped circulation reactor is composed of a tube, which serves as a reaction section and through which the reactants and the carbonate serving as reaction medium flow downwards, and of an external circulation, in which is situated a heat exchanger for cooling the circulated liquid to 50° C. The feed of the EOX or POX and the catalyst, dissolved in the corresponding carbonate, is carried out at the top end of the reaction tube in which is located a thin layer with ceramic rings as a mixing zone. The further mixing of the reactants in the reactor is effected by the pumped circulation. $CO_1$ is added at the bottom end of the reaction tube at a 6 to 7% excess, based on the alkylene oxide. The product stream from the pumped circulation reactor is conducted through a further tubular reactor which serves as a secondary reactor for completion of the conversion of the ethylene oxide and is likewise operated at 180° C. and 100 bar. This tubular reactor described has the disadvantage that, in addition to the in any case drastic conditions, temperature peaks can occur in the reaction section which have a product-damaging action. These temperature peaks, without particular precautions, can exceed 200° C. In order to counteract these temperature peaks, a high degree of back mixing is provided. The spatially adjacent metered addition of alkylene oxide and catalyst with simultaneously separate feed of the reaction panner $CO_2$ leads to high local excesses of alkylene oxide. This type of addition and back mixing in the reaction section favor the side reactions of the alkylene oxide and, in combination with the temperature peaks described, represent further disadvantages of these reaction conditions. Because the reaction of $CO_2$ with EOX or POX is highly exothermic, the reaction must be restricted in the first reactor and completed in a secondary reactor.

In the reactor described in Fette, Seifen (loc. cit.) and Chem. Ing. Techn. (loc. cit.), which is composed of a single tube without internals and without product circulation, $CO_2$ and EOX or POX are reacted together at 80 bar and 190° to 200° C. in the presence of a catalyst dissolved in the carbonate to be formed and the heat of reaction is removed with the aid of a heat transport medium circulating in counter-current which is in turn cooled by water. Even with this type of reaction conditions, peak temperatures are obtained of up to 220° C. in the reactor, which have a product-damaging effect, which is explicitly referred to in Fette, Seifen (loc. cit.); such temperature peaks are difficult to master, in particular in the case of an industrial plant. The entire heat of reaction is removed unutilized under these reaction conditions. Use would be achieved in a better manner through adiabatic reaction conditions, in which the entire heat of reaction liberated is absorbed by the reaction mixture itself. However, with exothermic reactions this always leads to an increase in the temperature of the reaction mixture, the harmful influence of which is referred to by the publications mentioned. Therefore, adiabatic reaction conditions are considered to be not technically realizable in Fette, Seifen (loc. cit.). As also in the process described further above, the conversion must be completed in a secondary reactor. Even in the reactor described without internals and without external product circulation, because of local alkylene oxide overconcentrations with respect to $CO_2$, side reactions of the alkylene oxide can take place which lead to a decrease in the selectivity of the reaction and thus to a decrease in the yield.

In the said German Offenlegungsschrift '232, various combinations of flow tubes and pumped circulation reactors which are operated at 10 to 50 bar and 100° to a maximum of 200° C. are described as reactor for the preparation of alkylene carbonates from alkylene oxides and $CO_2$. The carbonate to be formed serves in all reactor sections as reaction medium and represents there in each case 85 to 99.6% by weight of all substances present in the reactor. The starting materials $CO_2$ and alkylene oxide are metered into the first reaction zone of such a combination together with the catalyst dissolved in the carbonate to be formed. $CO_2$ is fed in this case only in a slight molar excess with respect to the catalyst. The components used for the reactor combinations used are stirred tanks, with external circulation for product cooling, and flow tubes. These reactor components, independently of their number and sequence within the combination, have in common that in them in each case only a partial conversion of the alkylene oxide can take place, since otherwise the heat problem of the highly exothermic reaction cannot be mastered. Only by such a complex connection of the reactors with coolers and execution of partial conversions can, in total, a conversion rate of alkylene oxide of about 99.5% and a carbonate selectivity of about 99% be achieved.

There was therefore the desire to have available a simple reactor, which can be enlarged to any scale, for the complete and selective reaction of alkylene oxides and $CO_2$ to give the associated alkylene carbonates, which can dispense with secondary reactors, complex cooling systems or a complex coupling of the reactor components and coolers. In such a reactor, moreover, the formation of harmful temperature peaks should be able to be avoided. A supplementary desire consists in the highest possible utilization of the exothermic heat of the reaction, for example in the context of the work-up of the reaction product or to generate process steam.

SUMMARY OF THE INVENTION

The invention relates to a reactor for the continuous preparation of ethylene glycol carbonate (EGC) or propylene glycol carbonate (PGC) from $CO_2$ and ethylene oxide (EOX) or propylene oxide (POX), respectively, in EGC or PGC, already present, as reaction medium in the form of a bubble column, characterized by a) a slenderness ratio as ratio of height to diameter of 2 to 80, preferably 2 to 50, especially preferably 5 to 30, b) a feed, at the bottom end of the bubble column, for the EGC or PGC, already present serving as reaction medium, c) one or more metering sites for the starting materials $CO_2$ and EOX or POX above the feed b), d) an outlet for the reaction mixture at the top end of the bubble column, e) a dividing device connected to d) for the reaction mixture flowing off for dividing it into reaction mixture (11) to be taken off and worked up and reaction mixture (10) to be recycled and f) a return line (10) and (3) to the feed b) for the reaction mixture to be recycled.

The reference numbers in brackets relate to the accompanying FIG. 1.

The invention further relates to a process for the continuous preparation of ethylene glycol carbonate (EGC) or propylene glycol carbonate (PGC) by reaction of ethylene oxide (EOX) or propylene oxide (POX), respectively, with 1.01 to 1.5 mol, preferably 1.01 to 1.4 mol, particularly preferably 1.01 to 1.35 mol, of $CO_2$ per mol of alkylene oxide in the temperature range from 100° to 200° C., preferably 100° to 190° C., particularly preferably from 110° to 180° C. and in the pressure range from 5° to 200° bar, preferably 5 to 80 bar, particularly preferably 8 to 60 bar in the EGC or PGC to be formed as reaction medium in an amount which is 7 to 350 bubble column react described above is used for the reaction. times that of the newly formed EGC or PGC, which is characterized in that a

BRIEF DESCRIPTION OF THE DRAWING

The accompanying

DETAILED DESCRIPTION OF THE INVENTION

Figure 1:
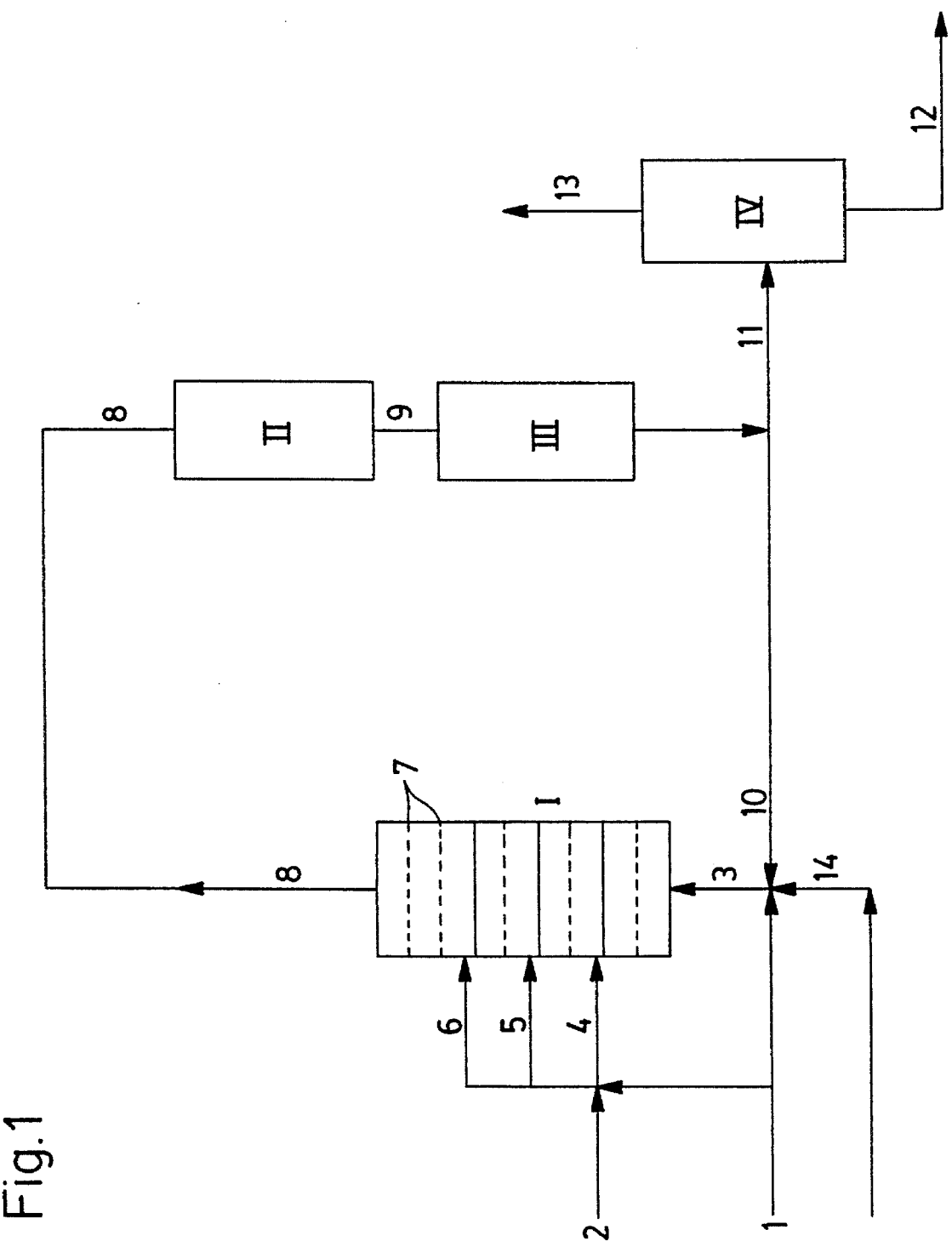
FIG. 1 shows the inventive reactor (I) completed by heat exchangers (II) and (III) and an expansion vessel (IV) to carry out the inventive process.

The starting materials EOX or POX and $CO_2$ are generally used at a purity of 99% and above. However, it is equally possible to use the starting substances at a lower purity if the remainder up to 100% is composed of inert substances, for example hydrocarbons, carbon monoxide or nitrogen. This applies particularly to $CO_2$, which can originate from various sources, for example from natural sources or from plants for generating water gas, carbon monoxide or reformers and is correspondingly of lower purity. However, such inert gases are expediently present in a proportion of no more than 10% by volume, preferably no more than 5% by volume, particularly preferably no more than 3% by volume.

The catalysts which can be used are virtually all those proposed previously, such as alkali metal bromides and alkaline earth metal bromides, alkali metal iodides and alkaline earth metal iodides, guanidine and hydrobromides or hydroiodides thereof, tetraalkylammonium bromides and tetraalkylammonium iodides, phosphonium bromides and phosphonium iodides, pyridinium halides, sulphonium halides, stibonium halides, arsonium halides, zinc halides, lead halides, alkyltin compounds or mixtures of alkali metal halides with halides of divalent metal ions. These catalysts are known to those skilled in the art and are not subject-matter of the invention. The catalysts used are preferably: alkali metal bromides and alkali metal iodides, tetraalkylammonium bromides and tetraalkylammonium iodides, phosphonium halides, guanidinium halides and mixtures of alkali metal halides with halides of divalent metals.

The reactor according to the invention and the process according to the invention to be carried out therewith are described below with reference to the accompanying FIG. 1. The reactor is essentially composed of a bubble column (I) which is provided with an external circulation. This bubble column can be insulated in a suitable manner for the preferred adiabatic process conditions. (I) is equipped with one, or preferably with a plurality of, metering sites for adding the starting materials $CO_2$ (1) and EOX or POX (2) into the EGC or PGC, respectively, serving as reaction medium and fed in at (3). In FIG. 1, three metering sites (4), (5) and (6) are depicted by way of example; further metering sites can be provided in an analogous manner. The higher number of metering sites, compared with only one metering site, contributes to the avoidance of local overconcentrations of EOX or POX and to the avoidance of local temperature peaks in the reactor.

It is further possible to feed $CO_2$ even beneath the bubble column into the EGC or PGC flowing in via (10) and (3). The starting substances are added conventionally and preferably in the gaseous state. The starting materials and the reaction medium fed in flow co-currently from bottom to top through (I). To further promote the reaction, (I) can preferably be provided with internals (7), as a result of which the structure of a cascaded bubble column results.

Internals for metering the starting substances and internals for ensuring a continuous good distribution and intensive mixing of all participating substances of the reaction mixture at all points in the reactor are for example perforated plates, perforated trays and baffle trays, pipe distributors (insert distributors and ring distributors), two-component nozzles, jet nozzles, nozzle trays, other nozzles, for example according to German Offenlegungsschrift 37 36 988 or German Offenlegungsschrift 37 44 001, gas introduction trays, sintered metal frits, closed gas distributor trays having through holes for the reaction medium, rotating gas introducers, impingement aerator elements, for example according to Perry's Chemical Engineers' Handbook 1984, pages 18.57 to 18.70, mixer elements, metal plate internals for increasing the turbulence, segmental and annular baffles. Such internals can also be used in combination with each other. In particular, such internals, apart from good mixing of the flow (macromixing) and the fine gas distribution, should generate as high a proportion as possible of high frequency turbulence elements in the dissipation region. Preferred internals are perforated trays, pipe distributors, two-component nozzles, jet nozzles, other nozzles, for example according to German Offenlegungsschrift 37 36 988 or German Offenlegungsschrift 37 44 001, closed gas distributors, impingement aerator elements and mixer elements.

To avoid undesirable temperature peaks and undesirable local overconcentrations, intensive mixing is maintained in the entire reactor composed of bubble column and external circulation.

(I) has a slenderness ratio as a ratio of height to diameter of 2 to 50, preferably 5 to 30; as a result the degree of backmixing within the bubble column is repressed.

This reduction in the backmixing of the bubble column is also supported by the above described internals.

However, a low degree of backmixing is desirable on the other hand because even with a single pass of the starting substances through the bubble column a virtually complete conversion of the alkylene oxide is to be achieved with an adequate mean residence time, which can be calculated theoretically and is to be verified by preliminary trials and is dependent on the type and concentration of the catalyst and on the conditions and on the reaction conditions.

This low degree of backmixing further favours the selectivity of the reaction of the alkylene oxide with the $CO_2$ to give the desired carbonate, since the side reactions of the alkylene oxides to form polycondensed aldehydes are a consequence of backmixing and poor mixing.

For the preferred case of a cascaded structure for the bubble column reactor, the distance between each two sequentially following internals for gas distribution is 0.1 to 10 times, preferably 0.3 to 8 times that of the bubble column diameter. This applies in the same manner to the further preferred case of a plurality of metering sites for the starting materials. In the case of these internals, the free gas introduction cross-section is dimensioned in such a way that a gas velocity of 0.1 to 15 m/s, preferably 0.2 to 12 m/s, results. For this purpose, the diameter of the boreholes in the internals is established at values from 0.2 to 20 mm, preferably 0.2 to 10 mm, particularly preferably 0.5 to 8 mm.

Taking into account the continuing absorption and reaction of the gaseous starting materials in the bubble column, the gas volume decreases in the flow direction. The free flow cross-section of the internals used for renewed gas distribution can therefore preferably decrease in the bubble column from bottom to top.

The reactor according to the invention is operated in the context of the process according to the invention to be carried out therewith in the temperature range from 100° to 200° C., preferably 100° to 190° C., particularly preferably 110° to 180° C. and at a pressure of 2° to 200° bar, preferably 5 to 80 bar, particularly preferably 8 to 60 bar; at temperatures in the upper part of the range given, pressures in the upper part of the range given are also used and vice versa. The adiabatic temperature increase in the process according to the invention is restricted to 2 to 80° C. The inlet temperature (I) is selected in this case such that even with full exploitation of the adiabatic temperature ,increase selected, the upper limit of the temperature range given is not exceeded for the entire reactor.

At all points of the reactor, a $CO_2$ excess over the EOX or POX is maintained. This excess is 1.01 to 1.5 mol, preferably 1.01 to 1.4 mol, particularly preferably 1.01 to 1.35 mol.

EGC or PGC as reaction medium is always present in the bubble column (I) in a great excess over the newly formed EGC or PGC. Thus per unit of time, 7 to 350 times the amount of EGC or PGC formed in this unit of time flows to the bubble column as circulation carbonate which also contains the catalyst. This great excess is further maintained in that 80 to 98% by weight, preferably 85 to 97% by weight of the total reaction mixture is returned to the entrance of the bubble column via the return line; only the remainder up to 100% of the reaction mixture is taken off and worked up to give pure EGC or PGC.

The process according to the invention is characterized in its preferred form by adiabatic temperature conditions. In this case, the reaction mixture is heated by the exothermic heat of reaction by 2° to 80° C. This sensible heat, inherent to the reaction mixture, can be utilized in various ways, cooling of the reaction mixture occurring again by 2° to 80° C. The most important of these possible methods of utilization is that for working up the reaction mixture to give pure EGC or PGC. For the case that the sensible heat achieved of the reaction mixture is very great, heating steam can furthermore still be produced which can be used for purposes other than those of the process according to the invention.

The reactor according to the invention is characterized by one or more metering sites for the gaseous starting substances $CO_2$ and EOX or POX. For the case of only one metering site, all gaseous starting materials are added together there. For the case of a plurality of metering sites, in principle $CO_2$ and EOX or POX can be added separately, the addition of $CO_2$ being preferably carried out before that of EOX or POX. However, in a preferred embodiment of the reactor according to the invention, all metering sites are connected in such a way that a joint addition of $CO_2$ and alkylene oxide is carried out. In a further preferred embodiment, additionally to the connection of the metering sites for the joint addition of $CO_2$ and alkylene oxide, a preliminary feed of $CO_2$ is provided into the return line (10) and (3). This preliminary feed of $CO_2$ includes in a further preferred manner the molar excess of $CO_2$ over the alkylene oxide, $CO_2$ and alkylene oxide being fed in as an equimolar mixture via the metering sites lying further above. This embodiment of the reactor ensures that $CO_2$ is always present in excess over the alkylene oxide and that is to say at all sites of the reactor. The number of metering sites for joint feed of $CO_2$ and alkylene oxide is 1 to 10, preferably 2 to 5. The number of the additional internals for distributing and mixing all participating substances, as described above, is 0 to 50, preferably 3 to 30; the FIG. 0 represents the case in which only metering sites/internals for $CO_2$ and alkylene oxide are present.

The majority of the reaction mixture flowing off from (I) is returned again to (I) via an external circulation (8), (9), (10) and (3). FIG. 1 shows heat exchange devices (II) and (III) in the course of this return line. For the case that the sensible heat inherent to the reaction mixture is used for the work-up of the reaction mixture and, in particular, for the case that this work-up is carried out by distillation, (II) can be the heating jacket of an evaporator for the reaction mixture to be worked up, for example a flash evaporator. (III) is given in FIG. 1 by way of example as a further heat exchanger, in which, for example, heating steam is generated. The arrangement of (II) and (III) is only given in FIG. 1 by way of example and can also be carried out in reversed sequence. Equally, a reactor to be heated of a completely different process, the reaction of which proceeds endothermically, can alternatively take the place of the heating steam-generating heat exchanger (III). The reaction mixture in the example of FIG. 1, after passage through (III), is divided into the part-streams (10) and (11). The pan-stream (10) includes in the manner described above 80 to 98% by weight of the total efflux of the bubble column (I); the part-stream (11) represents the remainder up to 100%. Obviously, it is possible in principle to perform the division into the part-streams (10) and (11) already between the heat exchangers (II) and (III) or already upstream of the heat exchanger (II).

While (10) is returned to the entrance of the bubble column, the part-stream (11) is fed to the work-up. For this purpose, (11) is first passed into a expansion vessel (IV), in which a separation into liquid (12) and gas (13) is performed. The gas phase (13) contains excess $CO_2$ and, possibly, traces of unreacted alkylene oxide and any inert gases introduced with the $CO_2$ and the alkylene oxide. Depending on the proportion of inert gases, a part-stream of (13) can be returned again into the reactor, while the remainder is fed to waste gas disposal. Clearly, with higher proportions of inert gas, a higher proportion of (13) is ejected to waste gas disposal and vice versa; simple analytical determinations and calculations as well as preliminary trials give without difficulty for those skilled in the art the optimum of the division of (13). The liquid (12) separated off in (IV) is fed to the isolation of pure product of EGC or PGC, for example by distillation.

The catalyst for the process according to the invention is fed into the return line (10) and (3) via (14). The amount of catalyst which is useful is that of 0.01 to 10% by weight, based on the circulating EGC or PGC. These amounts are dependent on the type of catalyst to be used; they are known to those skilled in the art and are not subject-matter of the present invention.

Some of the catalyst used leaves the process via (11) together with the reaction mixture to be worked up. This pan of the catalyst can be recovered during the work-up of the reaction product, regenerated as required and added back to the reactor (I) via (14). For the case that some of the catalyst must be ejected, this ejected part is supplemented by fresh catalyst via (14). As an example for the regeneration of exhausted catalyst, according to German Offenlegungsschrift 42 10 943, the treatment of catalysts of the type of mixtures of alkali metal halides with halides of divalent metals, for example $NaBr/ZnBr_2$, with halogen compounds, for example with hydrogen bromide, can be mentioned.

EXAMPLE

Into the reactor according to FIG. 1 operated at 16 bar, via (1), 0.275 kg of $CO_2$ and, via (2), 0.220 kg of EOX were metered in in total per hour, that is in such a way that 0.110 kg each of $CO_2$ and EOX flowed as a mixture through the lines (4) to (5) and 0.055 kg of $CO_2$ were added (3) to the reaction mixture of about 19.5 kg returning via (10) at a temperature of 120° C. before entry into the bubble column (I).

After the reaction has proceeded, 19.940 kg of reaction mixture having a temperature of approximately 135° C. left the reactor and flowed as a stream (8) into the heat exchangers (II) and (III). After this the temperature of the reaction mixture was about 120° C. The reaction mixture was then divided into the stream (10) of approximately 19.060 kg and (11) of approximately 0.880 kg. (10), as described, returned to the reactor, while (11) was depressurized in (IV) to 1 bar, the gaseous phase (13) and the liquid phase (12) being produced. (12) was passed into a falling film evaporator operated with the heat quantity from (II) and there split at about 15 mbar into 0.440 kg of vaporous EGC and 0.440 kg of bottom product.

After dividing this bottom product in the ratio 9:1, the greater part of 0.396 kg flowed directly back into the reactor and the smaller part of 0.044 kg flowed back into the reactor as catalyst solution (14), if required after regeneration.

The following parameters further underlay this example:

| Catalyst | $NaBr/ZnBr_2$ (molar ratio 2:1) |
| --- | --- |
| Catalyst concentration in the reactor | 0.3% by weight |
| Purity of EOX >99.5% | |
| Purity Of $CO_2$ >99.9% | |
| Type of internals for starting material feed | Pipe distributors |
| Type of internals for gas distribution | Perforated plates |
| Number of internals for gas distribution | 11 |
| Slenderness ratio of the bubble column | 35 |
| Volume of the bubble column | 0.64 l |
| Spacing of the internals for gas distribution (relative to the bubble column diameter) | 3.5 |
| Gas velocity in the boreholes of the internals for starting material feed for gas distribution and mixing | approximately 2.8 m/s (average; 2 to 7 m/s, depending on the position in the reactor) |

The EOX conversion rate over the entire reactor was 99.8%. The GC analysis of the crude carbonate showed 99.4 to 99.5% of EGC, that of the pure carbonate after distillation showed ≧99.6%.

What is claimed is:

1. A reactor for the continuous preparation of ethylene glycol carbonate (EGC) or propylene glycol carbonate (PGC) from $CO_2$ and ethylene oxide (EOX) or propylene oxide (POX), respectively, in EGC or PGC, respectively, already present as reaction medium, in the form of a bubble column, characterized by a) a slenderness ratio as ratio of height to diameter of 2 to 80, b) a feed, at the bottom end of the bubble column, for the EGC or PGC, already present serving as reaction medium, c) one or more metering sites for the starting materials $CO_2$ and EOX or POX above the feed b), d) an outlet for the reaction mixture at the top end of the bubble column, e) a dividing device connected to d) for the reaction mixture flowing off for dividing it into reaction mixture to be taken off and worked up and reaction mixture to be recycled and f) a return line and to the feed b) for the reaction mixture to be recycled.

2. A process for the continuous preparation of ethylene glycol carbonate (EGC) or propylene glycol carbonate (PGC) by reaction of ethylene oxide (EOX) or propylene glycol oxide (POX), respectively, with 1.01 to 1.5 mol of $CO_2$ per mol of the alkylene oxide in the temperature range from 100° to 200° C. and in the pressure range from 5 to 200 bar in the EGC or PGC to be formed as reaction medium in an amount which is 7 to 350 times that of the newly formed EGC or PGC, wherein a bubble column reactor with a) a slenderness ratio of height to diameter of 2 to 80, b) a feed, at the bottom end of the bubble column, for the EGC or PGC, already present serving as reaction medium, c) one or more metering sites for the starting materials $CO_2$ and EOX and POX above the feed b), d) an outlet for the reaction mixture at the top end of the bubble column, e) a dividing device connected to d) for the reaction mixture flowing off for dividing it into reaction mixture to be taken off and worked up and reaction mixture to be recycled and f) a return line to the feed b) for the reaction mixture to be recycled is used for the reaction.

3. The reactor of claim 1, having a slenderness ratio of 2 to 50.

4. The reactor of claim 3, having a slenderness ratio of 5 to 30.

5. The reactor of claim 1, having a cascading structure.

6. The reactor of claim 1, having internals in the form of perforated trays, pipe distributors, nozzles, two-component nozzles, jet nozzles, closed gas distributors, impingement aerator elements, mixer elements or a combination of a plurality of these.

7. The reactor of claim 6, having a spacing between two sequentially following internals of a value of 0.1 to 10 times that a diameter of the bubble column having a free gas introduction cross-section which permits a gas velocity of 0.1 to 15 m/s and having diameters for boreholes in the internals in the range from 0.2 to 20 mm.

8. The reactor of claim 7, having a spacing between two sequentially following internals of a value of 0.3 to 8 times that of the diameters of the bubble column.

9. The reactor of claim 7, having a free gas introduction cross-section which permits a gas velocity of 0.2 to 12 m/s.

10. The reactor of claim 7, having diameters for boreholes in the internals in the range from 0.5 to 10 mm.

11. The reactor of claim 10, having diameters for boreholes in the internals in the range from 0.5 to 8 mm.

12. The reactor of claim 1, having a free flow cross-section of the sequentially following internals decreasing from bottom to top.

13. The reactor of claim 1, having a feed line for $CO_2$ into the return line (10) and (3) of the returning EGC or PGC and 1 to 10 separate addition sites for the joint addition of $CO_2$ and EOX or $CO_2$ and POX.

14. The reactor of claim 13, having 2 to 5 separate addition sites for the joint addition of $CO_2$ and EOX or $CO_2$ and POX.

15. The process of claim 2, wherein an adiabatic procedure is carried out with a temperature increase in the reaction mixture between inlet and outlet of 2° to 80° C.

16. The process of claim 15, wherein the adiabatically stored heat of reaction in the reaction mixture is used to generate process steam or to work-up the ejected reaction mixture to give pure EGC or pure PGC, the reaction mixture cooling by a temperature of 2° to 80° C. and being returned in this form to the reactor entrance.

17. The process of claim 2, wherein 1.01 to 1.4 mol of $CO_2$ is reacted with one mol of the alkylene oxide.

18. The process of claim 17, wherein 1.01 to 1.35 mol of $CO_2$ is reacted with one mol of the alkylene oxide.

19. The process of claim 2, wherein the reaction is carried out in the temperature range of 100° to 190° C.

20. The process of claim 2, wherein the reaction is carded out in the pressure range of 5 to 80 bar.

* * * * *

UNITED STATES PATENT AND TRADEMARK OFFICE
CERTIFICATE OF CORRECTION

PATENT NO. : 5,508,442
DATED : April 16, 1996
INVENTOR(S) : Wagner, et al.

It is certified that error appears in the above-indentified patent and that said Letters Patent is hereby corrected as shown below:

Title Page      ABSTRACT: Line 4, 16, 19 & 21 delete " (EGG) " and substitute -- (EGC) --

Col. 10, line 19    Delete " carded " and substitute -- carried --

Signed and Sealed this

First Day of October, 1996

Attest:

BRUCE LEHMAN

Attesting Officer     Commissioner of Patents and Trademarks